(12) United States Patent
Maschke (10) Patent No.: US 8,252,049 B2
(45) Date of Patent: Aug. 28, 2012

(54) METHOD FOR THERAPY OF HEART VALVES WITH A ROBOT-BASED X-RAY DEVICE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 67 days.

(21) Appl. No.: 12/263,732

(22) Filed: Nov. 3, 2008

(65) Prior Publication Data

US 2010/0114308 A1 May 6, 2010

(51) Int. Cl.
*A61F 2/24* (2006.01)

(52) U.S. Cl. ........................ 623/2.11; 606/108

(58) Field of Classification Search .............. 623/1.11, 623/1.15, 2.11, 2.17, 2.37; 606/108
See application file for complete search history.

(56) References Cited

U.S. PATENT DOCUMENTS

| | | | |
|---|---|---|---|
| 4,819,751 A | 4/1989 | Shimada et al. | |
| 6,909,769 B2 * | 6/2005 | Bruder et al. | 378/8 |
| 2005/0085720 A1 * | 4/2005 | Jascob et al. | 600/424 |
| 2006/0020327 A1 * | 1/2006 | Lashinski et al. | 623/1.25 |
| 2006/0074485 A1 | 4/2006 | Realyvasquez | |
| 2007/0030945 A1 | 2/2007 | Boese et al. | |
| 2007/0173861 A1 | 7/2007 | Strommer | |
| 2009/0306500 A1 | 12/2009 | Rahn et al. | |

FOREIGN PATENT DOCUMENTS

| | | |
|---|---|---|
| DE | 10 2005 012 700 | 9/2006 |
| WO | WO 2004/103233 | 2/2004 |

OTHER PUBLICATIONS

S. V. Lichtenstein et al., "Transapical Transcatheter Aortic Valve Implantation in Humans Initial Clinical Experience", Circulation American Heart Association, 2006, pp. 591-596.
Cleveland Clinic, Heart & Vascular Institute, "Minimally Invasive Cardiovascular and Thoracic Surgeries", 2007, 6 pgs.
Robert S. Dieter, MD, "Percutaneous valve repair: Update on mitral regurgitation and endovascular approaches to the mitral valve", Applications in Imaging Cardiac Interventions, Oct. 2003.
Ted Feldman, M.D., "Percutaneous Valve Therapies: Where We Are and Where We Are Going", Complex Coronary Intervention, Jun. 2006.

* cited by examiner

*Primary Examiner* — Thomas J Sweet
*Assistant Examiner* — Seema Swaminathan
(74) *Attorney, Agent, or Firm* — Schiff Hardin LLP (57) ABSTRACT

A method or workflow for heart valve replacement, or more precisely emplacement of a prosthetic heart valve, using minimally invasive procedures includes imaging of the patient's heart during the procedure using a multi-access articulated x-ray imaging robot that allows a radiation detector carried by the robot to be moved in arbitrary paths around a patient in order to generate multiple projection exposures of the relevant region of the patient during the procedure. The imaging system is used to generate two dimensional image data during movement of the catheter and prosthetic heart valve into place and to generate three dimensional image data of the prosthetic heart valve within the patient's heart. The two dimensional image data and the three dimensional image data are registered and superimposed for use in positioning of the prosthetic heart valve. Additional imaging may be performed once the prosthetic heart valve is in position.

12 Claims, 8 Drawing Sheets

METHOD FOR THERAPY OF HEART VALVES WITH A ROBOT-BASED X-RAY DEVICE

BACKGROUND OF THE INVENTION

1. Field of the Invention

The present invention relates generally to a method for cardiological therapy and in particular to a method for using imaging during an interventional heart valve therapy using a robotic imaging device.

2. Description of the Related Art

The reduction of the pumping power of one or both heart chambers is generally designated as a cardiac insufficiency. Cardiac insufficiency is not an actual illness, but rather is the result of various diseases and/or pathology symptoms. As a result of cardiac insufficiency, the body and its organs do not receive the necessary amount of blood per unit of time. The vital organs are supplied with only an insufficient quantity of oxygen and nutrients.

Among the most important causes of cardiac insufficiency are illness of the coronary vessels (often the cause of extended infarctions), hypertension that is insufficiently medically regulated, heart muscle illness, heart muscle infection (myocarditis), illness of the pericardium, and illness of the heart valves. Illnesses of the heart valves are among the most important causes of cardiac insufficiency.

Congenital stenoses of one or more heart valves, or stenoses caused by other sources, such as, for example, calcium deposits, are frequent pathological conditions of the heart valves. In the case of a pulmonary valve stenosis, the leaflets of the pulmonary valve are thickened, so that the opening of the valve is hindered. The right chamber therefore works against an increased resistance, and forms more muscle mass, i.e. it becomes hypertrophic.

In aortic valve stenosis, a narrowing or constriction of the discharge path of the left chamber occurs. The cause is a thickening of the valvular cusp and/or an underdevelopment of the aortic root. The constriction may be below the valve (sub-valvular), at the valve (valvular) or above the valve (supra-valvular). The left chamber works against an increased resistance and becomes thicker (becomes hypertrophic). Sub-valvular and supra-valvular aortic stenoses can generally be treated using balloon catheters.

Mitral stenosis is normally an acquired valve defect, and is almost always the result of rheumatic endocarditis.

Until the 1990's, heart valve stenoses normally were therapeutically treated by open heart procedures. Such procedures have high risks associated therewith as well as long recovery (or convalescence) times for the patient.

The heart valves can be damaged by other illnesses, for example by inflammation, influenza or cardiac infarction, to the extent that the valve must be replaced or surgically modeled.

Various types of interventional surgical procedures are known for addressing one or more of the above causes of cardiac insufficiency. Until recently, a replacement of a heart valve required an open heart procedure. Mechanical or biological heart valve prostheses were implanted (to address issues with the aortic valve or pulmonary valve) or the existing valve opening was surgically shaped (to address issues with the mitral valve and tricuspid valve). Such procedures also were associated with high risks and long recovery times (up to six weeks) for the patient.

More recently, methods have been developed to treat heart valve stenoses in a minimally-invasive manner by the use of specially designed catheters. In principle, all four heart valves are accessible for a balloon dilation (referred to as valvuloplasty), but dilation of the tricuspid valve is only rarely implemented, due to the relative rarity of tricuspid stenosis.

The basic steps of a number of known balloon dilation procedures are described below.

For balloon dilation in the case of pulmonary valve stenosis, after probing of the right or left pulmonary artery from the groin with an open-ended catheter, a relatively rigid guide wire is introduced. A special dilation catheter (referred to as a valvuloplasty catheter) can be advanced via this guide wire after the catheter has been retracted.

This procedure is implemented under anesthesia, since filling of the balloon leads to a temporary interruption of circulation. In the case of less thickened valves, an excellent result with less residual resistance, and no or minimal insufficiency of the pulmonary valve, is achieved. In the case of a valve atresia, the targeted perforation of the valves by means of HF (High Frequency) energy and subsequent balloon dilation is frequently possible.

Balloon dilation in the case of aortic valve stenosis resembles the procedure for balloon dilation in the case of pulmonary valve stenosis, in that a balloon catheter is advanced via a guide wire to the location of the valve. Generally, the probing is implemented in a retrograde manner, since the left ventricle is accessible via the stenotic aortic valve.

For balloon dilation in the case of mitral stenosis, the balloon catheter can be inserted into the mitral valve either in an antegrade manner from the left atrium (after transseptal puncture) or in a retrograde manner from the left ventricle. More recently, the antegrade procedure has prevailed. The size (or area) of the opening (or aperture) of the mitral valve can be doubled, for example, by means of balloon dilation.

A catheter suitable for this purpose is described in U.S. Pat. No. 4,819,751. Such catheters have the advantage of allowing a minimally-invasive cardiac procedure to be conducted therewith.

For approximately two years, methods in clinical testing allow a replacement or modeling of heart valves in a minimally-invasive manner by the use of special catheters.

Integration of an artificial heart valve into a stent that is placed in the aortic valve and the pulmonary valve with a catheter is described, for example, in the Internet website www.corevalve.com or at or www.edwards.com. A detailed description can also be found in the article "Percutaneous Valve Therapies: Where We Are and Where We Are Going," by Feldman (available through the Internet site www.tct.com).

A suitable heart valve for this purpose is described in United States Patent Application Publication No. US 2006/0074485 A1.

The shape of the mitral valve and/or the valve opening thereof can be modeled with catheter-based tools, for example with the commercially available Carillon Mitral Contour System, available from the Internet site www.cardiacdimension.com. This catheter is conducted through the coronary sinus, and the procedure is known as percutaneous mitral annuloplasty.

A detailed description of known methods for repairing mitral valves can be found in the article "Percutaneous Valve Repair: Update on Mitral Regurgitation and Endovascular Approaches to the Mitral Valve," by Dieter.

A catheter device for insertion in an annuloplasty ring is described in PCT Published Patent Application WO 2004/103233.

In contrast to the above-described diseases, diseases of the tricuspid valve are rare, but when found to exist, can be treated in procedures similar to those described above concerning the mitral valve.

A significant disadvantage of all of the recently developed minimally-invasive procedures is that they must be implemented using x-ray fluoroscopy, which shows only a 2D (two-dimensional) image of the heart and the catheter and tools located therein or proximate thereto. It is very difficult for a surgeon or cardiologist to mentally form spatial associations from such 2D images.

A further disadvantage associated with such known procedures is that when the catheter is clearly visible in such an x-ray image, the opening of the heart valve in question is only poorly visible, or vice versa. The opening can be shown more clearly by the injection of a contrast agent, but a significant number of patients are at risk of having an allergic reaction to conventional contrast agents.

Due to these limitations in the content of the displayed images, a risk exists that the stenosis will not be correctly opened, or an artificial (replacement) heart valve may not be correctly placed.

It is also known to conduct some of these procedures, or portions thereof, supported by extracorporeal or intracorporeal (ICE, TEE) ultrasound imaging, but generally this does not provide a sufficient image quality.

Imaging in the context of the aforementioned known procedures could be improved by the use of a C-arm x-ray device, such as the CardDynaCT available from Siemens Medical Solutions. With this device, 2D (two-dimensional) soft tissue exposures as well as 3D (three-dimensional) high contrast exposures, typically obtained after the injection of a contrast agent, of a beating heart can be produced. However, the aforementioned commercially available C-arm x-ray device, as well as other commercially available C-arm x-ray devices, do not provide adequate access to the patient in order to permit percutaneous heart valve procedures to be implemented by operating personnel using known workflows or methods.

A method and apparatus for conducting an interventional procedure involving heart valves using a robot-based X-ray device is disclosed on co-pending U.S. patent application Ser. No. 12/046,727, filed on Mar. 12, 2008.

A multi-axis articulated robot suitable for use in the inventive method and apparatus is described in DE 10 2005 012 700 A1, the teachings of which are incorporated herein by reference. In that document, however, there is no mention or discussion of the use of such a robot imaging system for procedures involving heart valves.

Moreover, a procedure is described in United States Patent Application Publication No. 2007/0030945 wherein a 3D representation of the relevant anatomy of a heart, in particular soft tissue images, ensues with the use of ECG gating. The procedure described therein can operate with or without x-ray contrast agent for presentation of the relevant anatomy. Combined forms are also possible, meaning that exposures can be made with and without contrast agent and can be superimposed with each other or subtracted from one another. The teachings of United States Patent Application Publication No. 2007/00030945 are incorporated herein by reference.

SUMMARY OF THE INVENTION

The present invention provides a method for incorporating medical images including obtained using a radiation source and radiation detector mounted on a multi-axis articulated robot into a cardio intervention procedure. In particular, a method for performing a cardio intervention procedure, such as a heart valve replacement or heart valve surgical shaping, via a minimally invasive techniques while obtaining and using high definition three dimensional medical images in conjunction with two dimensional images. The three dimensional images are obtained at predetermined stages in the cardio intervention procedure to ensure correct valve insertion and placement.

The present invention also relates to a method and apparatus for movement of the imaging source and detector in predetermined paths for obtaining high resolution images during a cardio intervention procedure, such as a heart valve replacement, so as to generate images of use before, during and/or after the medical procedure. Movement through the predetermined movement paths of the imaging source and detector are possible when the source and detector are mounted on a multi-axis articulated robot. Such movement by the source and detector are possible prior to the cardio intervention, after the cardio intervention, and possibly even during the cardio intervention. By moving the source and detector about the patient, the patient may be kept stationary yet highly detailed images of the patient can be obtained to ensure that the cardio intervention will obtain the best result.

In the preferred embodiment, the method calls for the use of an x-ray device that is mounted on at least one multi-axis articulated robot for the cardio intervention, and in particular for therapy of heart valves via one or more minimally-invasive incisions in the thorax, on which multi-axis articulated robot is mounted a retention device with which the radiation source and the detector can be moved in arbitrary paths (advantageously in a circle, ellipse or spiral) around the patient in order to generate projection exposures, fluoroscopic and 3D x-ray exposures and for therapy planning, direction and monitoring.

The combination of a minimally-invasive interventional procedures of the type described and the use of the improved imaging system support provides many advantages beyond the separate application of these features. The patient need not be moved to a separate imaging location, a high definition three dimensional image of the relevant portions of the patient is available, and the imaging apparatus is not in the way while the medical professionals carry out the procedure.

DETAILED DESCRIPTION OF THE PREFERRED EMBODIMENTS

Figure 1:
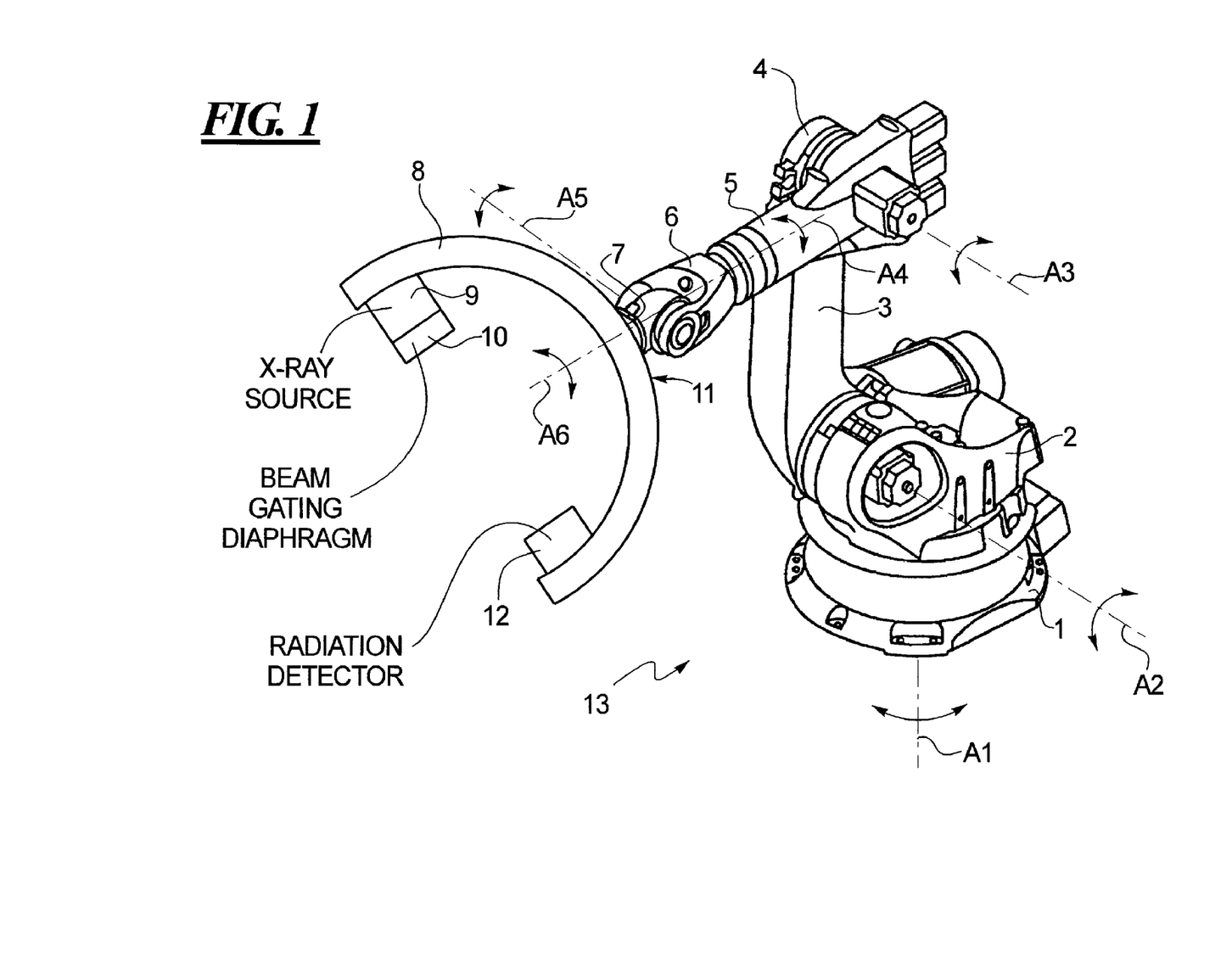
FIG. 1 in perspective view, shows a robot arm x-ray image acquisition system suitable for use in accordance with the inventive method system.

A method is provided for placing an artificial heart valve in a patient. The method of a preferred embodiment utilizes a robot arm x-ray image acquisition system 13 as shown in FIG. 1 of the type described in DE 10 2005 012 700 A1 for purposes other than implementing minimally invasive procedures involving heart valves. The robotic portion of the device 13 is mounted to a base 1 which, in this embodiment, is shown as a base affixed to the floor of a room in which the device 13 is used. The device 13, however, may also be wall-mounted or ceiling-mounted. A shoulder articulation 2 is rotatably mounted on the base 1, so as to be rotatable around a substantially vertical axis A1. The shoulder articulation is connected to a first arm portion 3 of an arm articulation, so that the first arm portion 3 is rotatable around a substantially horizontal axis A2. The first arm portion 3 is connected via an elbow articulation 4 to a second arm portion 5. The first arm portion 3 and the second arm portion 5 are rotatable relative to each other around a substantially horizontal axis A3 of the elbow articulation 4.

The second arm portion 5 carries a wrist articulation 6, which is rotatable relative to the second arm portion 5 around an axis A4. The wrist articulation 6 also includes a further articulation joint connected to a mount 7 for, in this embodiment, a C-arm 11. The holder 7 and the C-arm 11 connected thereto are rotatable around an articulation axis A5 in the wrist articulation 6, and the holder 7 and the C-arm 11 are also rotatable around a further articulation axis A6. The C-arm 11 includes a curved support 8, to which an x-ray source 9 and a radiation detector 12 are mounted for co-rotation with the support arm 8. A beam gating diaphragm 10 is disposed in front of the x-ray source 9, so as to be in the path of an x-ray beam that is emitted from the x-ray source 10 that propagates to the radiation detector 12. Alternatively, a beam gating diaphragm could be placed in proximity to the radiation detector 12.

The present method may be practiced with a variety of different imaging systems. In addition to an x-ray imaging system, the imaging system may be a combination x-ray and PET (positron emission tomography) imaging system, a combination x-ray and CT (computed tomography) imaging system, a combination x-ray and SPECT (single photon emission computed tomography) imaging system, and a combination x-ray and MRI (magnetic resonance imaging) system. Other imaging systems may be used as well.

Figure 2:
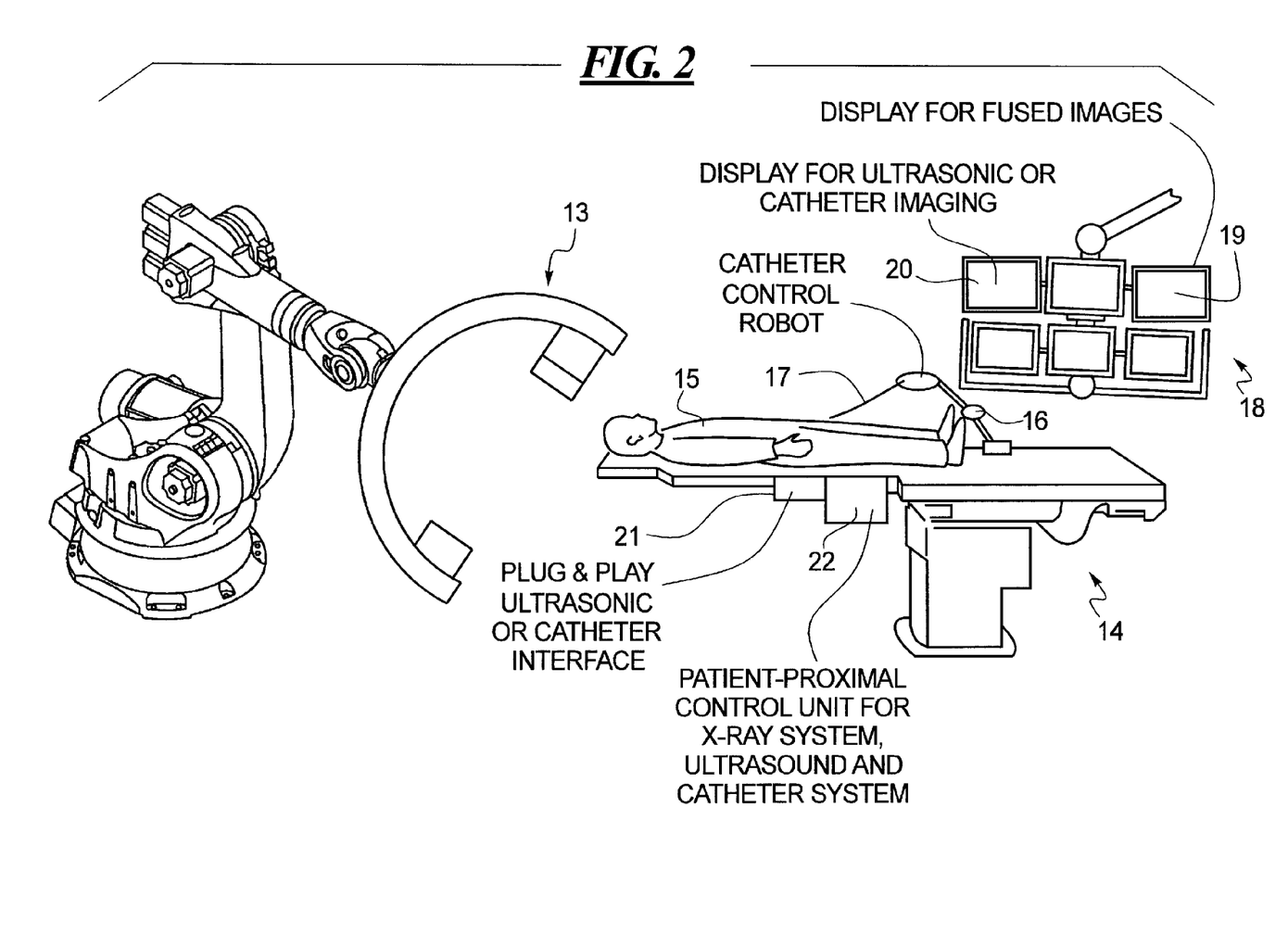
FIG. 2 illustrates the basic structural components of a system constructed and operating in accordance with the present invention.

As shown in FIG. 2, the robotic imaging device 13 is usable in combination with a table support 14 for a patient 15. Because of the numerous degrees of freedom provided by the robotic arm imaging device 13, and the non-restrictive access that is associated therewith, the system shown in FIG. 2 is suitable for implementing the various types of minimally-invasive procedures involving heart valves that were initially described. Many of these procedures require implementation of a catheter 17, which can be automatically or semi-automatically operated by a catheter control robot 16. A bank 18 of monitors or displays is provided that includes displays for separately displaying conventional types of images that are used in the aforementioned procedures. However, these displays include a display for fused images 19 and a display for ultrasonic or catheter imaging 20. One or more of the displays in the bank 18 can display a three-dimensional image that is generated from multiple projections of the region of interest of the patient 15 acquired by the robotic image acquisition system 13.

The system can be provided with a plug & play ultrasonic or catheter interface 21, if an ultrasound catheter is used. The system can also be provided with a patient-proximal control unit 22, for operating the x-ray system, the ultrasound system and the catheter system from a single location.

Figure 3:
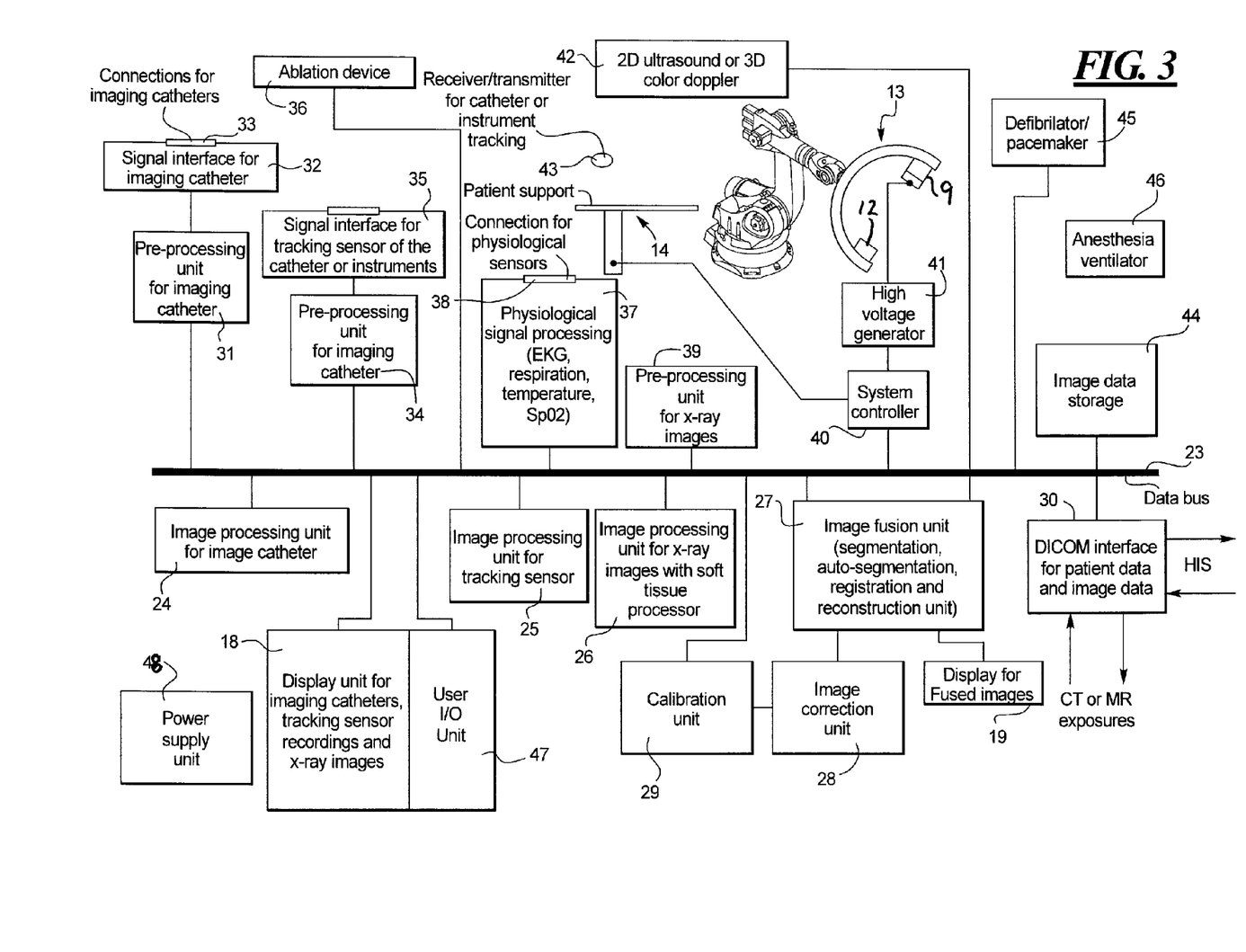
FIG. 3 is a detailed block diagram of an exemplary embodiment of the system of FIG. 2.

A more detailed block diagram presentation of the system of FIG. 2 is shown in FIG. 3. All components are connected to a data bus 23, which serves for transferring data as well as control instructions, as needed, between and among the various components.

These components include an image processing unit 24 for processing images obtained with an imaging catheter, such as an IVUS catheter or an optical catheter. Connected to the data bus 23 is also an image processing unit 25 for a tracking sensor that is associated with the image catheter, or another interventional instrument. Also connected to the data bus 23 is an image processing unit 26 for x-ray images, which includes a soft tissue processor, for generating images wherein soft tissue is accurately displayed. Also connected to the data bus 23 is an image fusion unit 27 connected to the aforementioned display for fused images 19. The data bus 23 is also in communication with a DICOM interface 30 for patient data, such as obtained from and transmitted to a hospital information system HIS, and for receiving and transmitting images such as CT exposures and/or MR exposures.

The image fusion 27 is capable of performing functions such as image segmentation, auto-segmentation, image registration and image reconstruction based on data supplied thereto, such as from the robotic imaging device 13 or from archived images received via the DICOM interface 30. The image fusion unit is connected to an image correction unit 28 which is, in turn connected to a calibration unit 29, the latter also being in direct communication with the data bus 23.

An image data storage 44 is also connected to the data bus 23, for storing any images generated during the minimally-invasive procedure involving heart valves, and for supplying images for display during that procedure, that have been previously obtained and stored.

Each of the image processing units 24, 25, 26, and the image fusion unit 27, and the image data storage 44 communicate with the display bank 18 (shown in FIG. 2) via the data bus 23. A user I/O unit 47 is also in communication with other components via the data bus 23. All units requiring power for operation thereof are supplied by a power supply unit 48.

Other components that will be most likely physically present in the operating room are shown above the data bus 23 in FIG. 3. In addition to the already-described robotic imaging device 13, these include a high-voltage generator 41 that supplies the necessary voltages and currents to the x-ray source 9, under the control of a system controller 40, which also operates the patient table 14.

A preprocessing unit 39 for processing the x-ray image data obtained from the radiation detector 12. For this purpose, the preprocessing unit 39 is in direct or wireless communication with the radiation detector 12.

A physiological signal processor 37 is provided for monitoring functions such as ECG, respiration, body temperature, blood oxygen concentration, etc. This processor 37 has an interface 38 for connection to appropriate physiological sensors.

A preprocessing unit 34 for processing image data from the imaging catheter is also connected to the data bus 23, which has a signal interface 35 for the tracking sensor of the catheter or other instruments.

Since more than one imaging catheter may be employed or more than one type of imaging catheter may be employed, FIG. 3 also shows a further preprocessing unit 31 for the imaging catheter, having a signal interface 32, and connections 33 to the imaging catheter.

If desired, the system may also be provided with an ablation device 36, which is connected to the data bus 23 so that it can be operated by the system controller 40. The same is true with regard to a defibrillator/pacemaker 45.

An extracorporeal ultrasound system 42 may also be provided, in the form of a 2D ultrasound system or a 3D color Doppler system, also connected to the data bus 23 so that it can be communicate with the image fusion unit 27.

For the aforementioned tracking of the catheter, catheters, or other instruments, a receiver/transmitter 43 is provided that can operate electromagnetically or according to any other known tracking mode.

An anesthesia ventilator 46 can also be provided with appropriate user interfaces and interfaces to the patient. Since such a unit is typically a stand-alone unit operated by an anesthesiologist, it is not shown as being connected to the data bus 23, although such a connection is possible, if desired.

Figure 4:
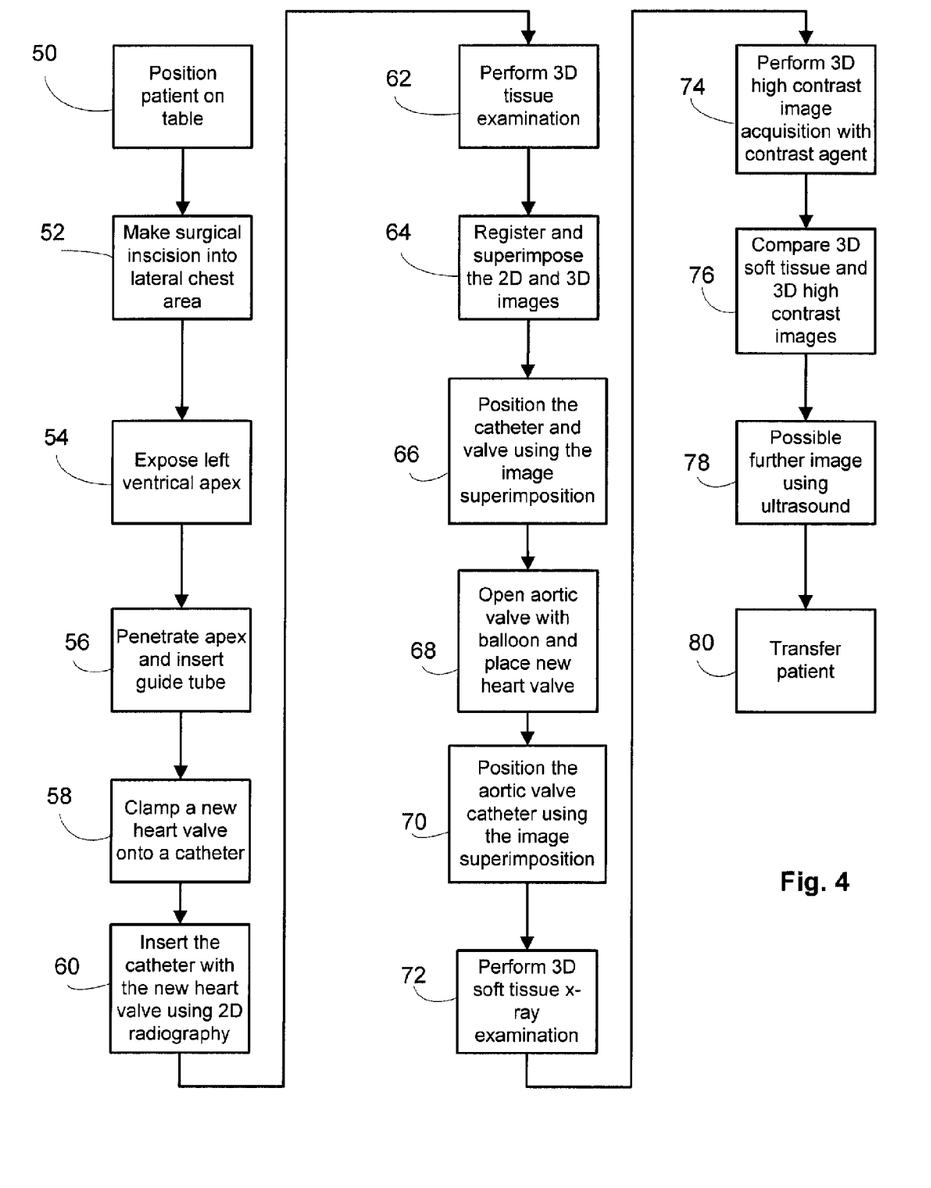
FIG. 4 is flow diagram illustrating a method or workflow according to a preferred embodiment of the present invention.

FIG. 4 illustrates an embodiment of the present method, in particular as an example of a transapical transcatheter workflow for implanting a heart valve, such as an artificial aortic valve, and integrating imaging into the implant process. The workflow with integrated imaging preferably uses an imaging system as shown in co-pending U.S. patent application Ser. No. 12/046,727, for example.

Once the medical professional has determined that the patient has a condition that requires replacement of an aortic heart valve and has readied the patient for the valve replacement procedure, the patient is positioned on the treatment table, as shown at step 50 in FIG. 4. The patient typically is placed on a gurney located outside the operating room and is thereafter moved into the operating room and transferred to the treatment table for the surgical procedure.

In step 52, a surgical incision is made in the side of the chest area of the patient and the replacement heart valve mounted on a catheter is inserted into the incision in the lateral chest area (termed a left anterolateral intercostal incision). In step 54, the medical professional exposes the left ventricular apex of the patient's heart. In step 56, the catheter is used to penetrate the left ventricular apex and insert a guide tube into the interior left ventricle of the patient's heart. In this step, a direct needle puncture of the apex is performed and a hemostatic sheath is introduced into the left ventricle.

The medical professional then clamps the new heart valve prosthesis onto a valvuloplasty catheter in step 58. In step 60, the valvuloplasty catheter with the mounted new heart valve prosthesis is inserted into the ventricle up to the old aortic valve under two dimensional (2D) x-ray radioscopy. The two dimensional radiography is performed using the C-arm multi-axis imaging apparatus, for example, that is in the operating room. In step 62, a three dimensional (3D) soft tissue x-ray examination of the prosthesis in the ventricle is performed using the same C-arm multi-axis imaging system in the operating room. The multi-axis imaging device is moved in pre-determined paths to obtain an image of the three dimensional structure of the soft tissues of the patient. The data of the three dimensional imaging is combined with the two dimensional image information in a 2D-3D registration and image superimposition step 64. This creates 2D-3D image superimposition data.

Next, the medical professional, in step 66, positions the valvuloplasty catheter with the mounted new heart valve prosthesis under two dimensional x-ray radioscopy on the basis of the 2D-3D image superimposition data. The superposed image data provides greater detail and information than would be available only using the relatively lower resolution two dimensional image data. It is not necessary for the medical professional to imagine the three dimensional structure of the patients heart while working with a two dimensional image, since the three dimensional soft tissue structure can be clearly seen in the superimposed image data. Once the prosthetic valve is in position, the medical professional operates the prosthesis expansion mechanism to cause dilation or, respectively, forcing open of the aortic valve, preferably with a valvuloplasty balloon, while turning and placing the new heart valve prosthesis into position using the catheter as the imaging system is operating to obtain two dimensional x-ray radioscopy images, in step 68. This placement of the valve results in the valve being located close to the desired position but is unlikely to result in the valve being in the optimum position for the valve, although it is possible that the placement step could locate the valve in the correct position.

According to step 70, the 2D-3D image superimposition data is examined and the aortic valve is re-positioned using the catheter based on the 2D-3D image superimposition data. The C-arm multi-axis imaging system is used to obtain the two dimensional image information used in this step. The imaging system is used again in step 72 to perform a three dimensional soft tissue x-ray examination in the area of the newly placed heart valve prosthesis. The positioning of the prosthesis in the patient's heart can be checked and a determination is made of whether the valve is in the optimum position.

In a further step 74, a contrast agent is provided into the patient's circulation system and the imaging system is used to perform a three dimensional high contrast image acquisition with the contrast agent. Issues relating to blood flow through and leakage around the newly placed valve prosthesis may be examined. In step 76, a comparison or, respectively, superimposition or subtraction of the three dimensional soft tissue exposure data and the three dimensional high contrast exposure data is prepared for monitoring of the attachment and function of the new heart valve.

Depending on the medical professional's practices and on the results of the above imaging and superimposition steps, the medical professional may request a concluding, extracorporeal ultrasound examination of the prosthesis in place, in step 78. This step may be skipped, if desired. The patient is transferred from the operating room, at step 80.

Figure 5:
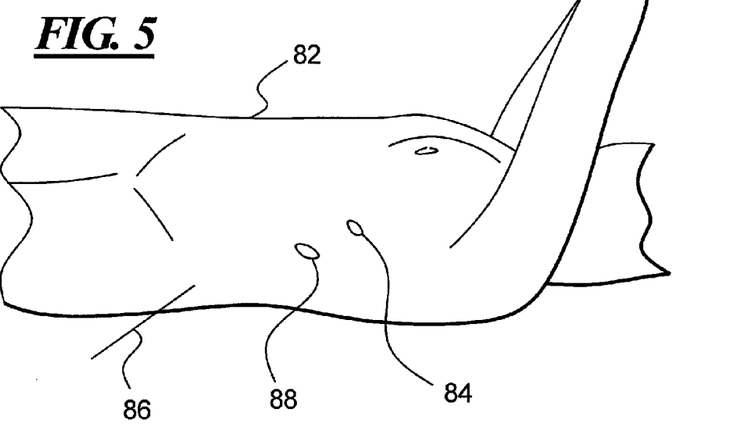
FIG. 5 is a side view of a patient torso showing a minimally invasive entrance.

Turning to FIG. 5, the patient's torso 82 is shown, lying prone on an operating table (not shown). A left anterolateral intercostal incision 84 has been made in the patient and a catheter 86 is about to be inserted into the incision 84. The catheter 86 includes a prosthetic heart valve 88 that is about to be placed inside the patient's heart. Other incision locations may be made instead.

Figure 6:
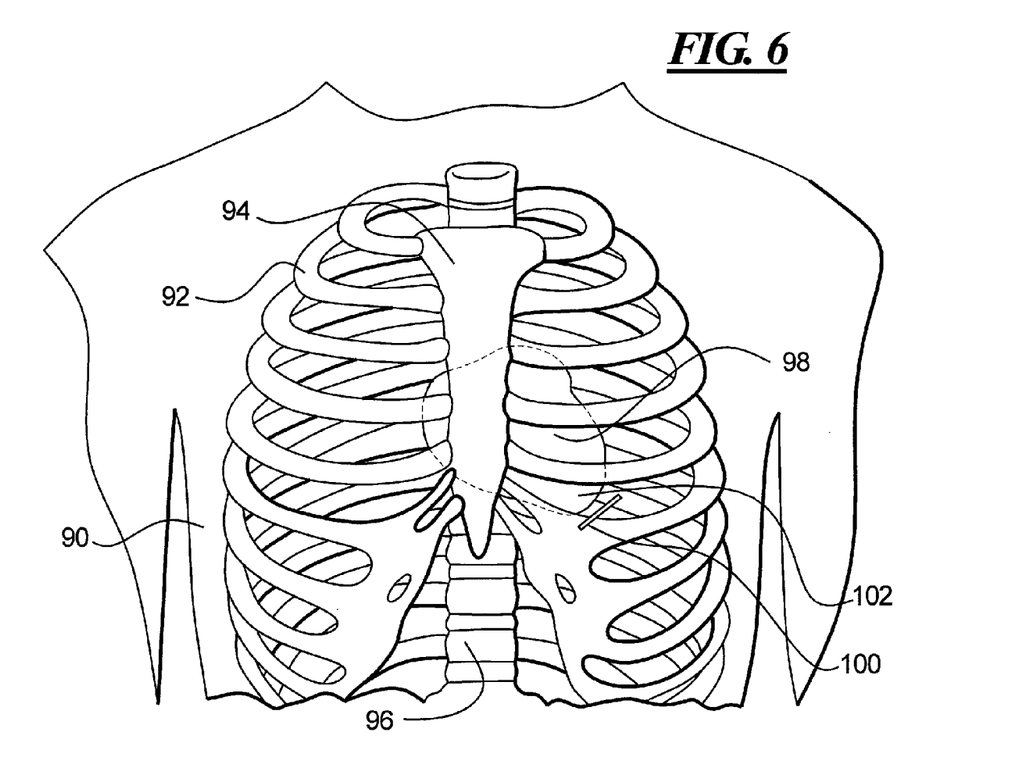
FIG. 6 is a plan view of a human heart relative to skeletal components and showing an incision location.

In FIG. 6, an image of the patient's chest cavity 90 including the rib cage 92, sternum 94, and spine 96, within which is located the patient's heart 98. An incision 100 for inserting the heart valve prosthesis into the chest cavity 90 is typically an intercostal incision, in other words, between the ribs. The incision 100 here is in the sixth intercostal space according to the preferred method. This locates the incision 100 within a short distance of the left ventricular apex 102 of the heart 98.

It is also possible that the incision may be made in the patient's inner thigh (for access to the heart via the saphenous vein), in the groin (for access via the femoral vein), or at the neck (for access via the jugular vein). Other entry points may be used as well.

Figure 7:
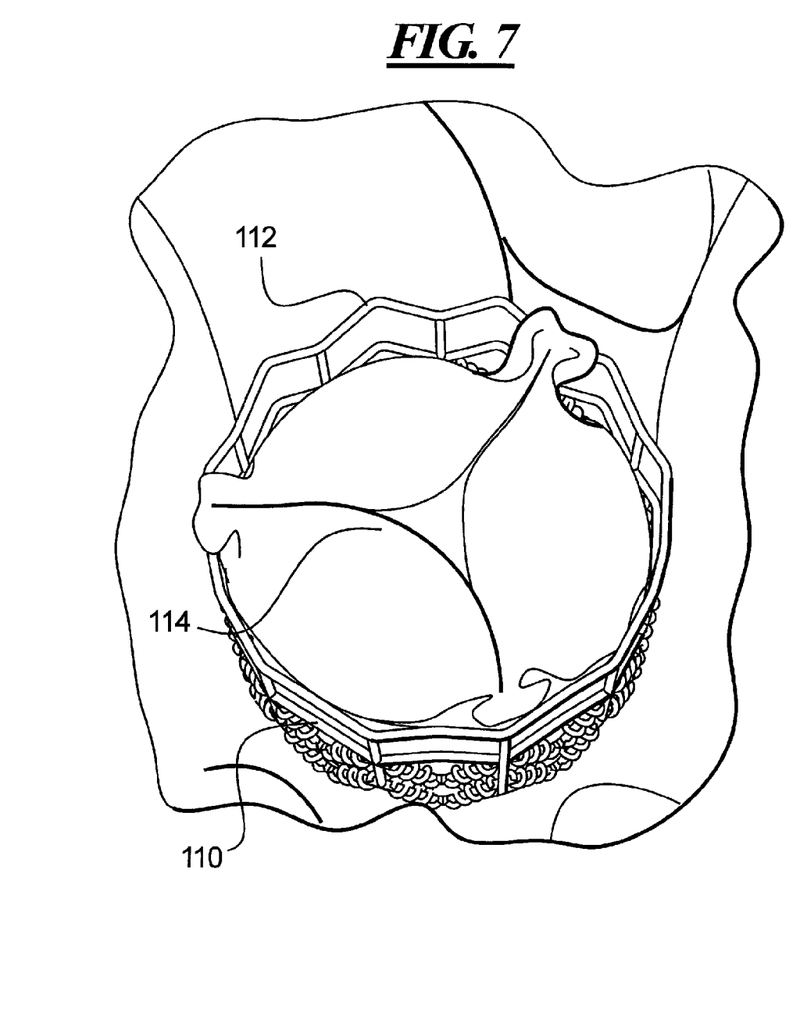
FIG. 7 is an end view of an artificial heart valve, or aortic bioprosthesis.

FIG. 7 is a heart valve prosthesis 110 shown in its expanded condition as it would appear in place within a patient's heart. The prosthesis includes an expandable frame or cage 112 and valve elements 114 of this tricuspid valve. The prosthesis 110 is initially provided in a crimped state wherein the diameter is significantly reduced to insertion, and once in place is expanded, such as by a balloon catheter. The illustrated prosthesis 110 is a Cribier-Edwards Aortic Bioprosthesis.

Figure 8:
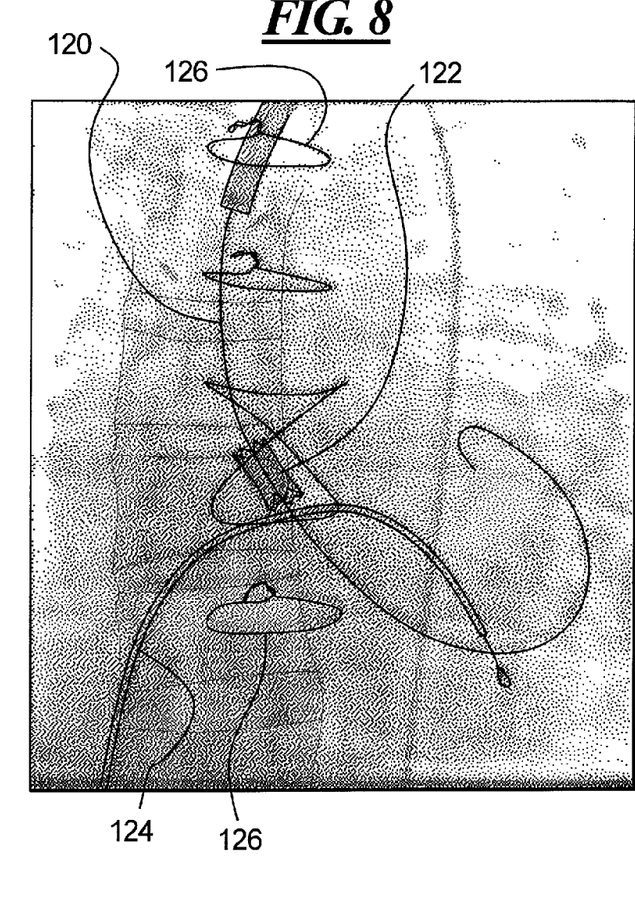
FIG. 8 is a medical image of a catheter emplacing an artificial heart valve in a patient.

FIG. 8 is an x-ray image of the patient's chest cavity in which a catheter 120 has been inserted into the patient's heart and a valve prosthesis 122 mounted on the catheter 120 is being moved into position while it its crimped state. An additional catheter 124 is seen in the x-ray, as well as reference elements 126. The x-ray image is a two dimensional image as obtained from x-ray radioscopy. The location of the prosthesis 122 relative to the heart structures is difficult to determine.

Figure 9A:
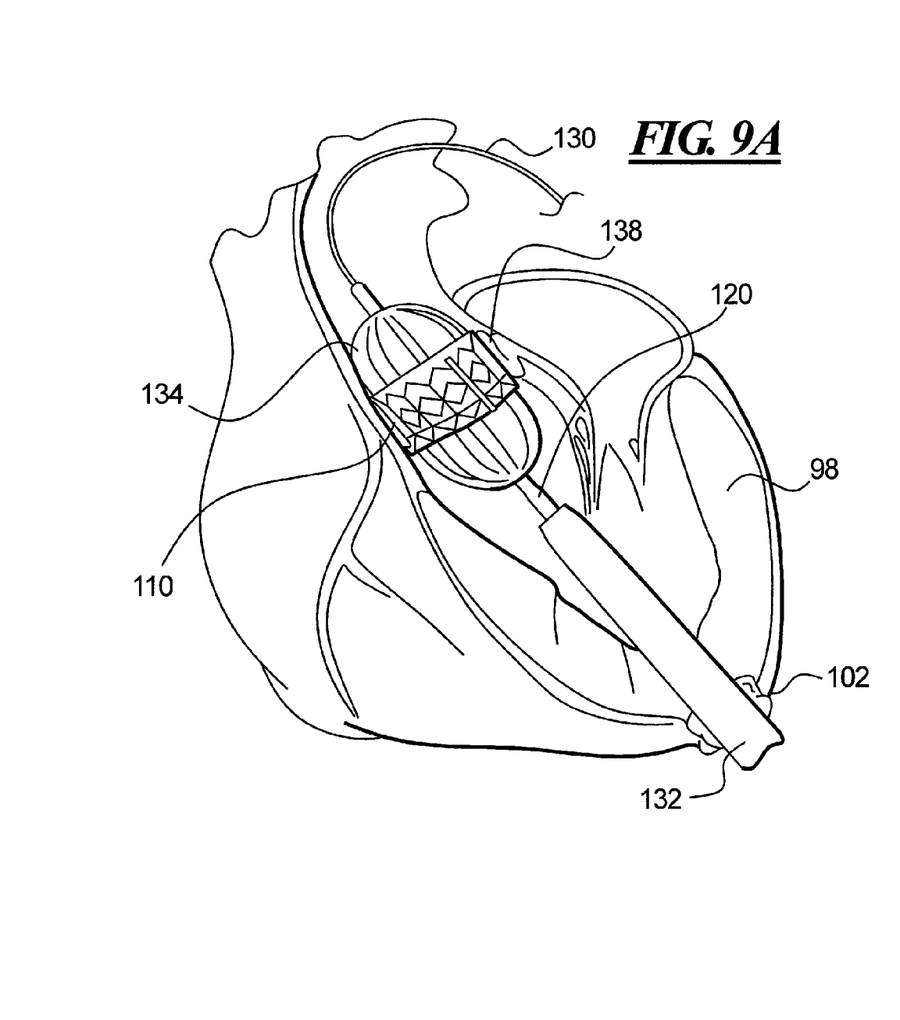
FIG. 9A is a cut away view of a human heart into which is being placed an artificial heart valve using a minimally invasive procedure.

FIG. 9A is an illustration of the heart 98 of the patient into which has been inserted a catheter 120 having the prosthesis 110 via the left ventricular apex 102. The catheter 120 has a guide wire 130 used for guiding the catheter into place, a lumen or sheath 132 along which the catheter is movable and which is used for opening and holding open the puncture in the ventricular apex 102, and a balloon 134 which has been expanded to expand the prosthesis 110 from the crimped or compressed state to the expanded state. The prosthesis 110 has been expanded at the position of the natural heart valve 138. The prosthetic heart valve must be accurately and securely placed, with little or no leakage around the edges and without interfering with heart function. Inspection of the prosthesis position prior to, during and after positioning is therefore of critical importance. The inspection during the procedure and between steps of the valve implacement procedure are possible without moving the patient using the C-arm multi-axis imaging system and the superimposed 2D and 3D image data.

Figure 9B:
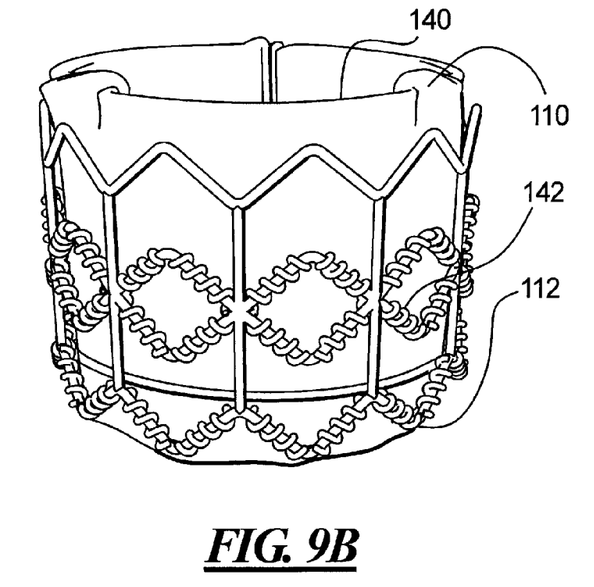
FIG. 9B is a view of the heart valve prosthesis of FIG. 9A.

FIG. 9B shows the heart valve prosthesis 110 including the cage 112 and membrane 140 that supports the valve elements 114 (see FIG. 7). The cage 112 includes anchor elements 142 to hold the prosthesis securely in position by engaging into the tissues of the heart.

Figure 10A:
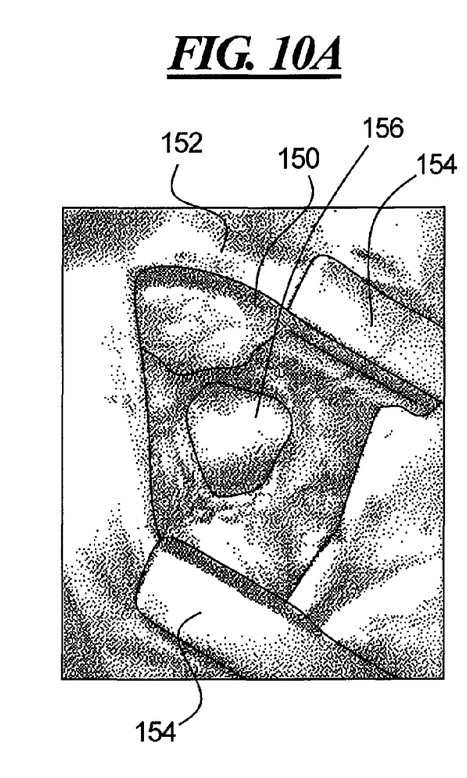
FIGS. 10A, 10B and 10C are a series of photographs showing a transapical aortic valve implantation, including exposure of the left ventricular apex in FIG. 10A, needle puncture to access the left ventricle in FIG. 10B, and use of a sheath to gain access to the aortic valve in FIG. 10C.
Figure 10B:
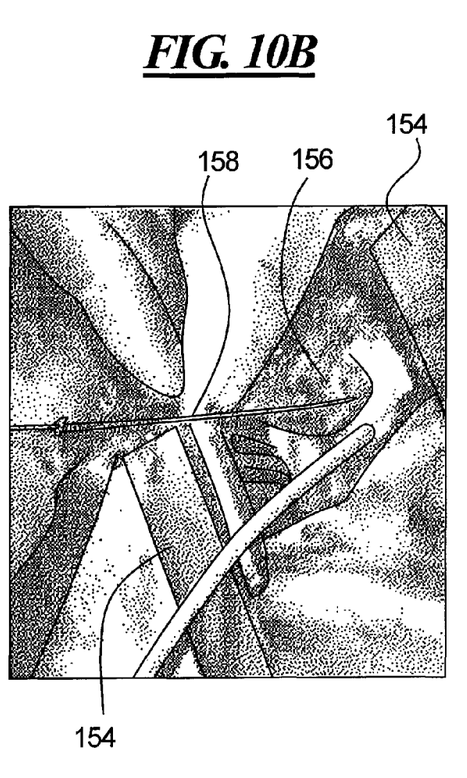
Figure 10C:
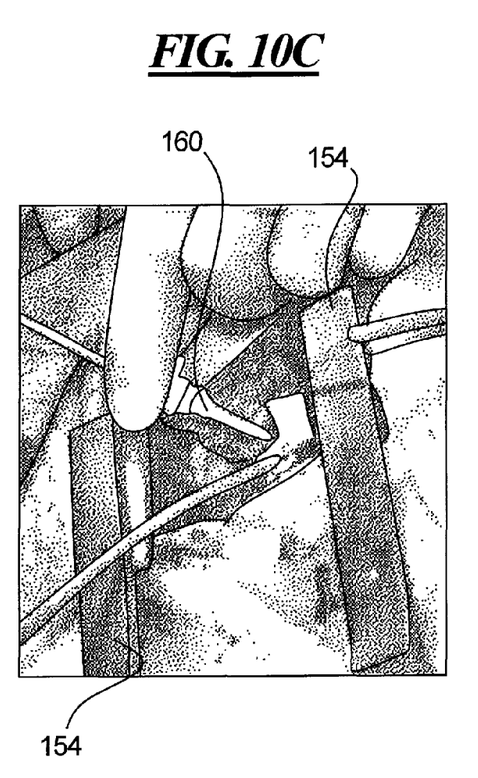

FIG. 10A shows a surgical procedure wherein an intercostal incision 150 has been made in the chest wall 152 of the patient in accordance with step 52 of FIG. 4 and retractors 154 placed to expose the left ventricular apex 156 of the heart as set forth in step 54. In FIG. 10B, a direct needle puncture is used to access the left ventricle 156. The ventricle 156 is pierced with a needle 158 according to step 56 of FIG. 4. In FIG. 10C, a standard sheath 160 is used to gain access to the aortic valve. Following the illustrated steps and the further steps described and show in FIG. 4, a transapical aortic valve implantation is accomplished.

The present workflow for valve implantation provides an improved medical workflow as well as a safer and faster therapy of valve illnesses in the heart of an organism.

The workflow utilizes and takes advantage of the multi-axis articulated x-ray imaging robot for conducting minimally-invasive procedures involving heart valves wherein a radiation detector carried by the robot to be moved in arbitrary paths, such as in circle, an ellipse, or along a spiral, around a patient in order to generate multiple projection exposures of the relevant region of the patient. The articulated robot has four degrees of freedom, and preferably has six degrees of freedom. 3D images, including 3D soft tissue images, can be reconstructed from the projection exposures obtained with the articulated robot x-ray imaging system. The points in time at which the respective projection exposures are generated can be registered, so that a 4D presentation can be reconstructed.

The robotic imaging device has at least one x-ray source and at least one x-ray detector. By manipulation of the robot arm the x-ray source can be positioned over or under the patient support (patient bed). It is also possible for the x-ray source to be mounted on a first robot and the x-ray detector to be mounted on a second robot. The robot arm or arms can be arranged on mobile carriers that allow flexible positioning in space by means of rollers, wheels, chain drive, etc. The movement in space of robot arm or arms can be accomplished by motorized actuators. The x-ray source and the detector can be mounted at the robot arm by a C-arm, a U-frame, or some other type of common holder. The base of the robot can be permanently mounted in the operating facility, such as on the ceiling, wall or floor of the operating room.

The patient support has an x-ray-transparent support surface, as is common. The supporting surface of the patient support can be spatially shifted manually, or in a motorized manner, in terms of height, longitudinal direction and transverse direction. The patient support can be floor-mounted, or can be supported by a further robot arm. The patient support can be tilted as needed in any of the x, y or z directions of a Cartesian coordinate system. The patient support can be rotatable around an isocenter. The patient support may additionally be able to execute circular or elliptical rotational movements around a fixed point in a plane, or a fixed point in space.

The basic components of the overall device are at least one x-ray tube with a radiation diaphragm, a patient table, a digital imaging system for fluoroscopic exposures, and system controller, a voltage generator, a radiation detector, as well as operating and display units. The x-ray detector is preferably an aSi detector. The operating units preferably allow operation using standardized selection possibilities, known as organ programs or examination programs. If an examination program (for example, aortic valve replacement) is selected, all system components, the image processing, the x-ray source, the radiation detector, and the table positions are automatically set by the system controller. A collision-avoidance unit or system can be provided that monitors critical positions of the movable components, and generates an alarm if and when a collision between components, or with operating personnel, is imminent, and may also prevent further movement after a limit range has been reached. A patient proximate operating unit can be provided that allows manual operation, supported by motors, of the robot arm by an operator. For this purpose, measurement sensors are connected into the robot arm that activate the motorized components or increase the motorized force, after exceeding a defined limit. A small, articulated robot can be provided to support or take over the guidance of the heart valve catheter. This small robot can be mounted in proximity to the patient.

An ultrasound device can additionally be integrated into the system, to which an extracorporeal transducer and an intracorporeal transducer can be connected for operation in a known manner. The x-ray exposures can be superimposed with the ultrasound exposures by an image fusion unit. Interfaces and image processing units can be provided to integrate further endoscopic or catheter-based image processing devices, such as any of OCT, IVUS, IVMRI, ICE or TEE, as well as to superimpose such images with the x-ray images. A device for spatial tracking of the catheter and instruments can be provided, such a tracking device operating with electromagnetic position sensors, as described in U.S. Pat. No. 5,042,486, or operating using ultrasound, as described in DE 198 52 467 A1. Additionally, an ablation device can be integrated into the system to implement ablation procedures at the heart valve, for example, HF procedures or cryo procedures.

A heart pacemaker unit can be provided to temporarily artificially beat the heart as needed. An anesthesia ventilator can also be provided in the system.

Thus, there is shown and described a method for performing a heart valve procedure using a multi-axis imaging system.

Although other modifications and changes may be suggested by those skilled in the art, it is the intention of the inventors to embody within the patent warranted hereon all changes and modifications as reasonably and properly come within the scope of their contribution to the art.

I claim:

1. A method for emplacement of a heart valve prosthesis in a patient's heart, comprising the steps of:
    positioning a patient on a table;
    accessing the patient's heart;
    penetrating a wall of the patient's heart to form an opening;
    inserting a catheter having a prosthetic heart valve mounted in a compact state on the catheter into the opening including inserting the prosthetic heart valve into the patient's heart;
    imaging the patient's heart using two dimensional imaging during insertion of the prosthetic heart valve to produce two dimensional image data;
    imaging the patient's heart using three dimensional imaging to produce three dimensional image data;
    registering and superimposing the two dimensional image data and the three dimensional image data to generate superimposed image data;
    imaging the patient's heart using two dimensional imaging during a positioning imaging step;
    positioning the prosthetic heart valve by positioning an image of the heart valve within the superimposed image data while imaging the patient's heart in said positioning imaging step;
    imaging the patient's heart using two dimensional imaging during an opening imaging step;
    opening the prosthetic heart valve to an expanded condition while in position in the patient's heart within the superimposed image data while imaging the patient's heart in said opening imaging step;
    imaging the patient's heart using three dimensional imaging to obtain a soft tissue image to determine a position of the prosthetic heart valve in the expanded condition in the patient's heart, said imaging step using three dimensional imaging to obtain a soft tissue image being performed without use of a contrast agent;
    imaging the patient's heart using a contrast agent to obtain high contrast image data of the expanded prosthetic heart valve in the patient's heart; and
    comparing the soft tissue image of the prosthetic heart valve in position with the high contrast image data to determine at least one of attachment and functioning of the expanded prosthetic heart valve.

2. A method as claimed in claim 1, further comprising the steps of:
    imaging the patient's heart with the expanded prosthetic heart valve using ultrasound imaging.

3. A method as claimed in claim 1, wherein said step of accessing the patient's heart includes:
    making a surgical incision into a lateral chest area of the patient;
    exposing a left ventricular apex of the patient's heart; and
    wherein said step of penetrating the wall of the patient's heart penetrates the left ventricular apex.

4. A method as claimed in claim 1, wherein said two dimensional imaging and said three dimensional imaging are performed using a multi-axis articulated imaging system.

5. A method for emplacement of a heart valve prosthesis in a patient's heart, comprising the steps of:
    positioning a patient on a table;
    accessing the patient's heart;
    penetrating a wall of the patient's heart to form an opening;
    inserting a catheter having a prosthetic heart valve mounted in a compact state on the catheter into the opening including inserting the prosthetic heart valve into the patient's heart;
    imaging the patient's heart using three dimensional imaging to produce three dimensional image data;
    imaging the patient's heart using two dimensional imaging during insertion of the prosthetic heart valve to produce two dimensional image data;
    registering and superimposing the two dimensional image data and the three dimensional image data to generate superimposed image data;
    position the prosthetic heart valve by positioning a current position of the prosthetic heart valve obtained by two-dimensional imaging within the superimposed image data;
    opening the prosthetic heart valve to an expanded condition while in position in the patient's heart;
    imaging the patient's heart using three dimensional imaging to obtain soft tissue image data to determine a position of the prosthetic heart valve in the expanded condition in the patient's heart; said imaging step using three dimensional imaging to obtain a soft tissue image being performed without use of a contrast agent
    imaging the patient's heart using a contrast agent to obtain high contrast image data of the expanded prosthetic heart valve in the patient's heart; and
    comparing the soft tissue image data and the high contrast image data to determine at least one of an attachment and functioning of the prosthetic heart valve in the patient's heart.

6. A method as claimed in claim 5, further comprising the steps of:
    imaging the patient's heart with the expanded prosthetic heart valve using ultrasound imaging.

7. A method as claimed in claim 5, wherein said step of accessing the patient's heart includes:
    making a surgical incision into a lateral chest area of the patient;
    exposing a left ventricular apex of the patient's heart; and
    wherein said step of penetrating the wall of the patient's heart penetrates the left ventricular apex.

8. A method as claimed in claim 5, wherein said two dimensional imaging and said three dimensional imaging are performed using a multi-axis articulated imaging system.

9. A system for emplacement of a heart valve in a patient's heart, comprising:
    an imaging system selected from the group consisting of an x-ray imaging system, a combination x-ray and PET (positron emission tomography) imaging system, a combination x-ray and CT (computed tomography) imaging system, a combination x-ray and SPECT (single photon emission computed tomography) imaging system, and a combination x-ray and MRI (magnetic resonance imaging) system; the system being operable to perform the method steps of:

imaging the patient's heart using two dimensional imaging during insertion of a prosthetic heart valve to produce two dimensional image data;

imaging the patient's heart using three dimensional imaging to produce three dimensional image data, either prior to or following the two dimensional imaging step;

registering and superimposing the two dimensional image data and the three dimensional image data to generate superimposed image data;

imaging the prosthetic heart valve during positioning within the patient's heart;

displaying the prosthetic heart valve within the superimposed image data during the positioning;

imaging the patient's heart using three dimensional imaging to obtain soft tissue image data to determine a position of the prosthetic heart valve after the heart valve is in the expanded condition in the patient's heart; said imaging step using three dimensional imaging to obtain a soft tissue image being performed without use of a contrast agent imaging the patient's heart using a contrast agent to obtain high contrast image data to determine a position of the prosthetic heart valve after the heart valve is in the expanded condition in the patient's heart; and comparing the soft tissue image data and the high contrast image data to determine at least one of attachment and functioning of the prosthetic heart valve in the patient's heart.

10. A method as claimed in claim 1, wherein said comparing step includes at least one of comparing, superimposing and subtracting the soft tissue image data and the high contrast image data.

11. A method as claimed in claim 5, wherein said comparing step includes at least one of comparing, superimposing and subtracting the soft tissue image data and the high contrast image data.

12. A system as claimed in claim 9, wherein said comparing step includes at least one of comparing, superimposing and subtracting the soft tissue image data and the high contrast image data.

* * * * *